US007662554B2

(12) United States Patent
Cantor et al.

(10) Patent No.: US 7,662,554 B2
(45) Date of Patent: Feb. 16, 2010

(54) NUCLEIC ACID SUPPORTED PROTEIN COMPLEMENTATION

(75) Inventors: Charles R. Cantor, Del Mar, CA (US); Natalia E. Broude, Natick, MA (US); Carlos Witte-Hoffmann, Boston, MA (US)

(73) Assignee: The Trustees of Boston University, Boston, MA (US)

( * ) Notice: Subject to any disclaimer, the term of this patent is extended or adjusted under 35 U.S.C. 154(b) by 52 days.

(21) Appl. No.: 10/529,122

(22) PCT Filed: Oct. 9, 2003

(86) PCT No.: PCT/US03/32426

§ 371 (c)(1),
(2), (4) Date: Sep. 29, 2005

(87) PCT Pub. No.: WO2004/033485

PCT Pub. Date: Apr. 22, 2004

(65) Prior Publication Data

US 2006/0094014 A1    May 4, 2006

Related U.S. Application Data

(60) Provisional application No. 60/417,323, filed on Oct. 9, 2002, provisional application No. 60/478,803, filed on Jun. 16, 2003.

(51) Int. Cl.
C12Q 1/68 (2006.01)
G01N 33/53 (2006.01)

(52) U.S. Cl. ........................................... 435/6; 435/7.1

(58) Field of Classification Search ................. 435/6, 435/7.1
See application file for complete search history.

(56) References Cited

U.S. PATENT DOCUMENTS

| 5,654,195 | A | * | 8/1997 | Sodroski et al. | 435/320.1 |
| 5,728,527 | A | * | 3/1998 | Singer et al. | 435/6 |
| 5,795,718 | A | * | 8/1998 | Eisenbeis | 435/6 |
| 5,854,033 | A | * | 12/1998 | Lizardi | 435/91.2 |
| 6,270,964 | B1 | | 8/2001 | Michnick et al. | |
| 6,287,772 | B1 | * | 9/2001 | Stefano et al. | 435/6 |
| 6,294,330 | B1 | | 9/2001 | Michnick et al. | |

(Continued)

FOREIGN PATENT DOCUMENTS

WO    WO-03/025220 A2    3/2003

(Continued)

OTHER PUBLICATIONS

Beach, Dale L. et al.; Current Biology; 9(11):569-578 (1999).

(Continued)

Primary Examiner—Kenneth R. Horlick
(74) Attorney, Agent, or Firm—Morrison & Foerster, LLP

(57) ABSTRACT

The present invention is directed to novel methods for in vitro and in vivo detection of target nucleic acid molecules, including DNA and RNA targets, as well as nucleic acid analogues. The present invention is based on protein complementation, in which two individual polypeptides are inactive. When the two inactive polypeptide fragment are brought in close proximity during hybridization to a target nucleic acid, they re-associate into an active, detectable protein.

24 Claims, 5 Drawing Sheets

Protein complementation supported by nucleic acid interactions

U.S. PATENT DOCUMENTS

| | | | |
|---|---|---|---|
| 6,428,951 | B1 | 8/2002 | Michnick et al. |
| 6,730,474 | B1 * | 5/2004 | van Dongen et al. ............ 435/6 |
| 2002/0049174 | A1 | 4/2002 | Stocks et al. |
| 2002/0064779 | A1 | 5/2002 | Landegren et al. |
| 2003/0049688 | A1 | 3/2003 | Michnick et al. |
| 2003/0124629 | A1 | 7/2003 | Tse et al. |
| 2005/0272107 | A1 | 12/2005 | Rabbitts et al. |
| 2005/0276800 | A1 | 12/2005 | Rabbitts et al. |

FOREIGN PATENT DOCUMENTS

| | | | |
|---|---|---|---|
| WO | WO-03/025220 | A3 | 3/2003 |
| WO | WO-2004/046189 | A2 | 6/2004 |
| WO | WO-2004/046189 | A3 | 6/2004 |

OTHER PUBLICATIONS

Bertrand, Edouard et al.; Molecular Cell; 2:437-445 (Oct. 1998).

Birkenmeyer, Larry G. et al.; Journal of Virological Methods; 35:117-126 (1991).

Carmo-Fonseca, Maria et al.; Critical Reviews in Eukaryotic Gene Expression; 9(3&4):213-219 (1999).

Landegren, Ulf; Trends Genetics; 9(6):199-204 (1993).

Matsuo, Toshihiko; Biochimica et Biophysica ACTA; 1379:178-184 (1998).

Pederson, Thoru; Nucleic Acids Research; 29(5):1013-1016 (2001).

Perlette, John et al.; Anal. Chem.; 73:5544-5550 (2001).

Zubritsky, Elizabeth; Anal. Chem.; 73:657A (2001).

St. Johnson, Daniel; Cell; 81:161-170 (Apr. 21, 1995).

Tsuji, Akihiko et al.; Biophysical Journal; 81:501-515 (Jul. 2001).

Molenaar, C. et al. (2001). "Linear 2' O-Methyl RNA Probes for the Visualization of RNA in Living Cells," *Nucleic Acids Res.* 29(17):e89:1-9.

Oleynikov, Y. et al. (Feb. 4, 2003). "Real-Time Visualization of ZBP1 Association with β-Actin mRNA during Transcription and Localization," *Current Biology* 13:199-207.

Pelletier, J.N. et al. (Oct. 1998). "Oligomerization Domain-Directed Reassembly of Active Dihydrofolate Reductase from Rationally Designed Fragments," *Proc. Natl. Acad. Sci. USA* 95:12141-12146.

Politz, J.C. (Jul. 1999). "Use of Caged Fluorochromes to Track Macromolecular Movement in Living Cells," *Trends Cell Biol.* 9:284-287.

Sando, S. et al. (Aug. 21, 2002; e-pub. Jul. 31, 2002). "Imaging of RNA in Bacteria with Self-Ligating Quenched Probes," *J. Am. Chem. Soc.* 124(33):9686-9687.

Sei-Lida, Y. et al. (2000). "Real-Time Monitoring of In Vitro Transcriptional RNA Synthesis Using Fluorescence Resonance Energy Transfer," *Nucleic Acids Res.* 28(12);e59:i-vii.

Sokol, D.L. et al. (Sep. 1998). "Real Time Detection of DNA•RNA Hybridization in Living Cells," *Proc. Natl. Acad. Sci. USA* 95:11538-11543.

Tsuji, A. (Jun. 2000). "Direct Observation of Specific Messenger RNA in a Single Living Cell under Fluorescence Microscope," *Biophys. J.* 78(6):3260-3274.

Wherman, T. et al. (Mar. 19, 2002). "Protein-Protein Interactions Monitored in Mammalian Cells Via Complementation of β-Lactamase Enzyme Fragments," *Proc. Nat. Acad. Sci. USA* 99(6):3469-3474.

Tse, E. et al. (Oct. 24, 2000) "Intracellular Antibody-Caspase-Mediated Cell Killing: An Approach for Application in Cancer Therapy," *PNAS* 97(22):12266-12271.

* cited by examiner

Protein complementation supported by nucleic acid interactions

Protein-complementation assay supported by triplex DNA formation and applied in RCA

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
cgactgcgtt agcatgtgtt g                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
gctgacgcaa tcgtacacaa c                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
caacacatgc taacgcagtc g                                              21
```

NUCLEIC ACID SUPPORTED PROTEIN COMPLEMENTATION

CROSS-REFERENCE TO RELATED APPLICATIONS

This application is a 371 National Phase Entry Application of co-pending International Application PCT/US2003/032426, filed 9 Oct. 2003, which designated the U.S. and which claims the benefit under 35 U.S.C. §119(e) of U.S. Provisional Applications 60/478,803, filed 16 Jun. 2003, and 60/417,323, filed 9 Oct. 2002.

This application claims benefit under 35 U.S.C. §119(e) of U.S. Ser. No. 60/417,323 filed Oct. 9, 2002 and U.S. Ser. No. 60/478,803 filed Jun. 16, 2003.

FIELD OF THE INVENTION

The present invention provides a method for in vivo and in vitro detection of nucleic acid targets, including DNA and RNA targets.

BACKGROUND OF THE INVENTION

There is a great demand for methods to detect and quantify the presence of a target nucleic acid sequence of interest. In particular, there is a great demand for methods that can be used to detect and quantitate the presence of a target nucleic acid in vivo and in vitro.

For example, detection of RNA in vivo is of particular interest. During the last several years, knowledge on multiple functional roles of RNAs in gene expression has substantially increased, as has the number of newly isolated RNA molecules. Additionally, it has become clear that mRNA localization plays an important role in directing specific proteins to their correct position within the cell, thus regulating gene expression and cell development (Johnston, 1995; Oleynikov & Singer, 2003). To fully understand functions of various RNAs, methods of studying their dynamic behavior within living cells are required.

Different strategies for labeling RNA molecules for in vivo detection have been used (for a review, see Pederson, 2001). Most methods rely on different RNA-specific hybridization probes and microinjection or lipofection for probe delivery to the nucleus or cytoplasm. For example self-ligating quenching probes were successfully used by Kool and co-workers for RNA hybridization within bacterial cells (Sando & Kool, 2002). Fluorescent 2-O-methyl-RNA probes have been shown to be more stable than unmethylated oligonucleotides and have been used by several groups (Carma-Fonseca et al, 1999; Molenaar et al., 2001). Molecular beacons, (Sokol et al., 1998; Perlette & Tan, 2001), RNA hybridizing oligonucleotide probes capable of fluorescence resonance energy transfer (FRET) (Matsuo, 1998; Tsui et al., 2000; Tsuji et al, 2001; Sei-Iida et al., 2000) and caged-fluorescein labeled antisense oligonucleotides present different variants of the same approach (for a review see Politz, 1999, Pederson, 2001).

However, all of these approaches are probe-based, and thus are limited by the low sensitivity of hybridization due to the low concentration of RNA within the cell. In most cases, only highly abundant RNA species can be detected. Thus, because of their abundance, it has been possible to detect β-actin mRNA, c-fos mRNA, basic fibroblast growth factor RNA, and total poly (A)-RNA).

Another obstacle of using oligonucleotide probes for RNA detection in vivo is their fast accumulation in the nucleus (Tsuji et al., 2000; Molenaar et al., 2001). One approach to overcome this difficulty has been the use short oligonucleotide hybridization probes bound to streptavidin via biotin-straptavidin interactions, to lower their passage through nuclear pores (Tsuji et al., 2000).

Yet another strategy to study RNA in vivo has been to generate fusions between functionally important RNA-binding proteins and fluorescent proteins, which allows RNA kinetic studies. For example, real time RNA movement in yeast cells was monitored by co-expressing a GFP-MS2 fusion protein and an ASH1 RNA reporter fused to MS2 binding sequences (Bertrand et al, 1998; Beach et al., 1999; Oleynikov & Singer, 2003). In these studies, GFP or its spectral variants were used as fluorescent tags. Thus, no signal amplification was generated in this approach, which again restricts the method to detection of only highly abundant RNAs. Another drawback of this approach is the background signal of the expressed fluorophore-protein chimera, which substantially limits the sensitivity of the method.

The majority of detection methods have relied on the use of nucleic acid probes to detect a nucleic acid of interest. Probe-based assays are useful in the detection, quantitation and analysis of nucleic acids. Nucleic acid probes have long been used to analyze samples for the presence of nucleic acid from bacteria, fungi, virus or other organisms and are also useful in examining genetically-based disease states or clinical conditions of interest. Nonetheless, probe-based assays have been hampered in part by difficulties associated with specificity, sensitivity and reliability, and the challenges presented by detection of nucleic acids in vivo.

Nucleic acid hybridization is a fundamental process in molecular biology. Sequence differences as subtle as a single base (point mutation) in very short oligomers (<10 base pairs "bp") can be sufficient to enable the discrimination of the hybridization to complementary nucleic acid target sequences as compared with non-target sequences. However, nucleic acid probes of greater than 10 bp in length are generally required to obtain the sequence diversity necessary to correctly identify a unique organism, disease state or clinical condition of interest.

Several nucleic acid probe-based methods have been developed for the detection of nucleic acids. Most are designed around the amplification of selected targets and/or probes composed of DNA, including the polymerase chain reaction (PCR), ligase chain reaction (LCR), self-sustained sequence replication (3SR), nucleic acid sequence based amplification (NASBA), strand displacement amplification (SDA), amplification with Q.beta. replicase (Birkenmeyer and Mushahwar, J. Virological Methods, 35:117-126 (1991); Landegren, Trends Genetics, 9:199-202 (1993)), rolling circle amplification (RCA), and linear rolling circle amplification (LRCA), which uses a primer annealed to the circular target DNA molecule before adding DNA polymerase.

However, these methods are associated with a number of difficulties, including relatively low precision in quantitative measurements, being laborious, expensive, time-consuming, inefficient, and lacking in sensitivity. In addition, there are sources of error in such methods, such as where structural differences lead to different efficiencies.

Any hybridization of a nucleic acid probe to a closely related non-target sequence will result in the generation of undesired background signal. Because the sequences are so closely related, point mutations are some of the most difficult of all nucleic acid modifications to detect using a probe-based assay. Numerous diseases, such as sickle cell anemia and cystic fibrosis, are caused by a single point mutation of genomic nucleic acid.

Furthermore, all of these methods suffer from a lack of sensitivity, especially to rare genetic events, such as infrequent mutations.

In addition, the detection of nucleic acids in vivo, including in real time, has presented a significant challenge. For example, demonstrating hybridization between an antisense oligonucleotide and its mRNA target has proven extremely difficult in living cells. The development of molecular beacon technology has provided one new approach to nucleic acid detection in vivo. See Sokol et al., Proc. Natl. Acad. Sci. USA 95:11538-43 (1998); Perlette et al., Anal. Chem. 73:657A (2001).

Accordingly, it would be highly desirable to have improved methods for the detection of target nucleic acids, including methods for in vivo detection. Such improved detection of DNA and RNA targets would be useful in the detection, analysis and quantitation of nucleic acid containing samples.

SUMMARY OF THE INVENTION

The present invention is directed to methods for in vitro and in vivo detection of target nucleic acid molecules, including DNA and RNA targets, as well as nucleic acid analogues. In the method of the present invention, a target nucleic acid is detected by its binding to a complementation complex, wherein the complementation complex comprises a first complementation molecule and a second complementation molecule. The first complementation molecule comprises a first polypeptide portion coupled to a first probe portion, which specifically interacts with the target nucleic acid; the second complementation molecule comprises a second polypeptide portion coupled to a second probe portion, which specifically interacts with the target nucleic acid in close proximity to the first probe. Binding of both probe portions to the target nucleic acid brings the first complementation molecule and the second complementation molecule into close proximity, such that they are able to interact and form an assembled complementation complex, which can be detected by any means which allows recognition of the assembled complex but not the individual polypeptides.

The target nucleic acid can be detected in vivo or in vitro. The target nucleic acid can be single-stranded or double-stranded.

In one preferred embodiment of the invention, the first and second polypeptides interact in the complementation complex to form an assembled, active enzyme, which can be detected using an enzyme activity assay. Preferably, the enzyme activity is detected by a chromogenic or fluorogenic reaction. In one preferred embodiment, the enzyme is dihydrofolate reductase or β-lactamase.

In another preferred embodiment of the invention, the first and second polypeptides interact in the complementation complex to form an assembled protein with detectable fluorogenic activity. In one preferred embodiment, the assembled protein is green fluorescent protein (GFP) or a modified GFP such as EGFP, or any other natural or genetically engineered fluorescent protein such as CFG, YFP, or RFP.

In another preferred embodiment of the invention, the first and second polypeptides interact in the complementation complex to form an assembled protein which contains a discontinuous epitope, which may be detected by use of an antibody which specifically recognizes the discontinuous epitope on the assembled protein but not the partial epitope present on either individual polypeptide.

The first probe portion and the second probe portion may be any molecules which interact specifically with a target nucleic acid in close proximity. In one preferred embodiment, the probes are nucleic acids or nucleic acid analogues, such as oligonucleotides. In a further embodiment of the present invention, one or both of the probe portions is a nucleic-acid binding polypeptide, which interacts with the target nucleic acid with high affinity.

In another preferred embodiment, the polypeptide portion of the molecule is coupled to the probe portion of the complementation molecule such that when the probe portions of the first molecule and the second complementation molecules are bound to the target nucleic acid, the two polypeptides of the first and second complementation molecules can interact. For example, a flexible linker can be used to couple the probe portion and the polypeptide portion of the complementation molecule. In one preferred embodiment, the N-terminal amino acid and/or the C-terminal amino acid of each polypeptide is cysteine, and the probe has a thiol group at the 3' or 5' end, to allow coupling to the N-terminal and/or C-terminal cysteine.

In one preferred embodiment, the target nucleic acid can be amplified prior to exposure to the components of the complementation complex. For example, rolling circle amplification (RCA) can be used to generate a single-stranded DNA target with a multiplicity of the same hybridization sites, which bind to the probes of the complementation complex.

In one particularly preferred embodiment, the first and the second probes bind to two adjacent sequences on the target nucleic acid, such that the first probe binds to a first target sequence and the second probe binds to a second target sequence. In this embodiment, the adjacent sequences are close enough to each other to allow the first and second polypeptides to interact when the first and second complementation molecules are bound to the target, allowing assembly of the complementation complex. This embodiment provides for detection of single-stranded and double-stranded target nucleic acids. For detection of double stranded targets, the single-stranded probes interact with the double-stranded target to form a triplex.

In another particularly preferred embodiment, the first and the second probes are oligonucleotides and bind to the same sequence on a single-stranded target nucleic acid, forming a triplex. In this embodiment, the first and second polypeptides interact when the first and second complementation molecules are bound to the target, allowing assembly of the complementation complex.

In embodiments providing for formation of a triplex, the probe can be an oligonucleotide or a polypeptide. Preferred triplex-forming oligonucleotides are GC-rich. A preferred triplex is a purine triplex, consisting of pyrimidine-purine-purine.

One embodiment of the present invention provides in vivo detection of target nucleic acids. In this embodiment, interaction of the first and second polypeptides can be detected in vivo. For example, using a fluorogenic protein such as GFP or EGFP, which can be detected in living cells, or using a chomogenic substrate via an enzyme such as beta-galactosidase.

In one embodiment, the present invention provides a method of detecting the presence and/or quantity of target nucleic acid present in a sample. A sample containing a target nucleic acid is contacted under hybridization conditions with the components of the complementation complex, namely the first molecule and the second molecule. The presence and/or quantity of the assembled protein is indicative of the presence and/or quantity of the target nucleic acid.

The present invention also provides methods for isolating a target nucleic acid in a sample, even in the presence of non-target sequences.

In another preferred embodiment, the present invention provides kits suitable for detecting the presence and/or amount of a target nucleic acid in a sample. Said kits comprise at least the components of the complementation complex, namely a first probe coupled to a first molecule and a second probe coupled to a second molecule, wherein the probes can bind to a target nucleic acid in close proximity. Said kits also comprise reagents suitable for capturing and/or detecting the present or amount of target nucleic acid in a sample. The reagents for detecting the present and/or amount of target nucleic acid can include enzymatic activity reagents or an antibody specific for the assembled protein. The antibody can be labeled.

BRIEF DESCRIPTION OF THE DRAWINGS

FIG. 2A: Buffer F (20 mM Tris-Cl ph 8.0, 50 mM NaCl, 0.1% Triton X-100). FIG. 2B: Purified EGFP (11.4 nM) FIG. 2C: Alpha and Beta fragments from a mock conjugation reaction without DNA FIG. 2D: Alpha hybrid containing oligonucleotide B1 mixed in equal volume (7.5 µl) with Beta hybrid containing a parallel complementary oligonucleotide B2. FIG. 2E: Alpha hybrid containing oligonucleotide B1 mixed in equal volume (7.5 µl) with Beta hybrid containing an antiparallel complementary oligonucleotide (APB2). FIG. 2F: Mixture of complementary parallel oligonucleotide (B1-B2)(20 µM) without proteins. FIG. 2G: Mixture of complementary antiparallel oligonucleotide (B1-APB2) (20 µM) without proteins.

FIG. 3A: Buffer. FIG. 3B: Alpha hybrid containing oligonucleotide B1 mixed in equal volume (7.5 µl) with Beta hybrid containing a parallel complementary oligonucleotide (B2) diluted ½0. FIG. 3C: Alpha hybrid containing oligonucleotide B1 mixed in equal volume (7.5 µl) with Beta hybrid containing a parallel complementary oligonucleotide (B2) diluted ½0. FIG. 3E: Alpha hybrid containing oligonucleotide B1 mixed in equal volume (7.5 µl) with Beta hybrid containing an antiparallel complementary oligonucleotide (APB2) diluted ½0. FIG. 3E: Alpha hybrid containing oligonucleotide B1 mixed in equal volume (7.5 µl) with Beta hybrid containing an antiparallel complementary oligonucleotide (APB2) diluted ½0.

As shown in FIG. 4A, due to complementary interactions, two inactive protein fragments come in close contact and undergo conformational changes, restoring enzymatic activity, which is detected by a chromogenic or fluorogenic reaction. Different types of complementation complexes can be used in this approach. FIG. 4B shows the use of DNA duplexes. FIG. 4C shows duplex and triplex formation by nucleic acid mimics. Finally, the inactive protein fragments can be fused to DNA- or RNA-recognizing peptides, which interact with target DNA or RNA with high affinity. These interactions will also bring two inactive protein fragments in close contact, restoring activity and thus signaling the presence of the target nucleic acid.

FIG. 5A depicts synthesis of single-stranded RCA product with triplex-forming regions. FIG. 5B depicts an in vitro assay to test the restoration of the DHFR activity (or β-lactamase activity).

DETAILED DESCRIPTION OF THE INVENTION

Figure 1:
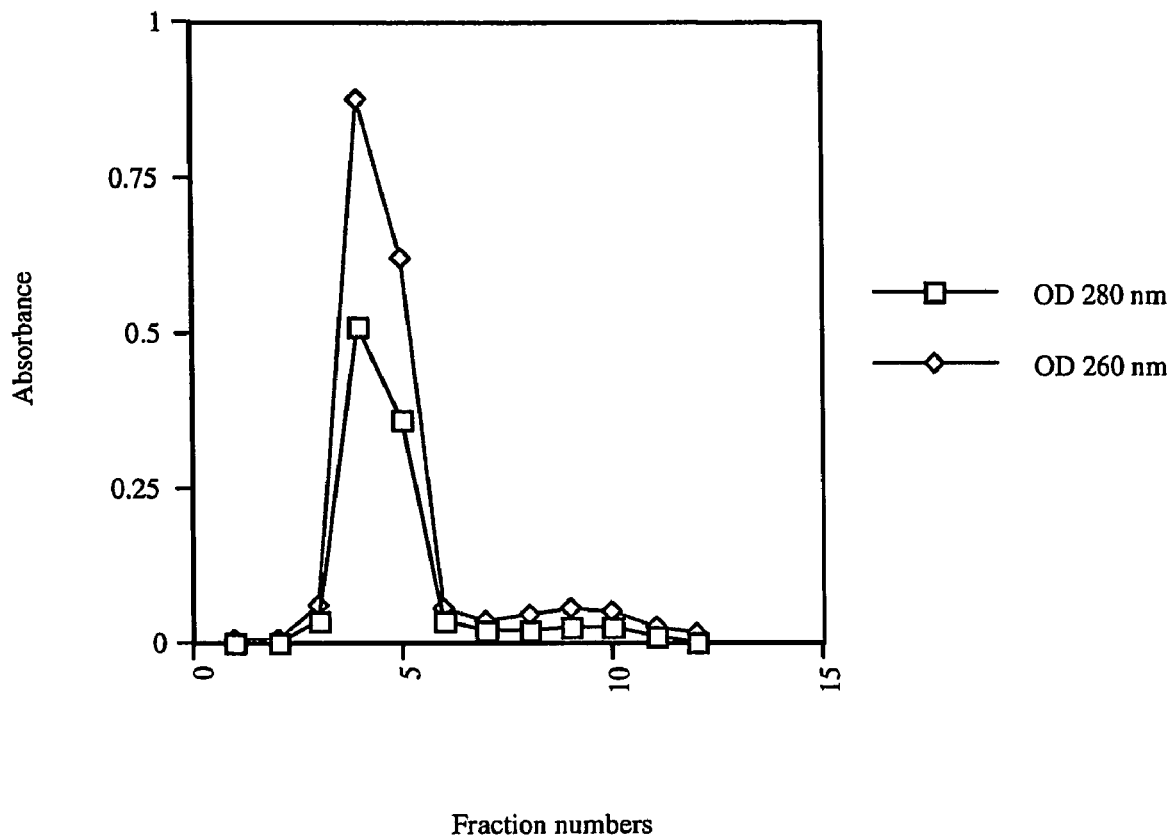
FIG. 1 shows the chromatographic profile of a conjugation mixture (Alpha-cys plus oligonucleotide B1) on a Sephadex G-25 column. Alpha-cys fragment (1.6 uM) was mixed with oligonucleotide B1 (50 uM) in 500 ul of buffer M (50 mM HEPES pH 7.0, 0.5 M NaCl, 1 mM EDTA, 10 mM DTT, 0.5 mM PMSF, 10 mM Tris-Cl) and left on ice for 34 hrs. Afterwards, the sample was applied by gravity flow to a G-25 Sephadex column (NAP-5, Pharmacia) equilibrated with buffer C (50 mM HEPES pH 7.0, 0.5 M NaCl, 1 mM EDTA, 0.5 mM PMSF). Fractions (~0.17 ml)) were collected at room temperature.

We have now discovered methods to improve the specificity, sensitivity and reliability of probe-based assays both in vivo and in vitro. Such improved detection of DNA and RNA targets is useful in the detection, analysis and quantitation of nucleic acid containing samples.

The present invention is based on protein complementation, in which two individual polypeptides are inactive. When the two inactive polypeptide fragments are brought in close proximity, however, they are able to re-associate into an active protein.

The present invention is directed to methods for in vitro and in vivo detection of target nucleic acid molecules, including DNA and RNA targets, as well as nucleic acid analogues. In the method of the present invention, a target nucleic acid is detected by its binding to a complementation complex, wherein the complementation complex comprises a first complementation molecule and a second complementation molecule. The first complementation molecule comprises a first polypeptide portion coupled to a first probe portion, which specifically interacts with the target nucleic acid; the second complementation molecule comprises a second polypeptide portion coupled to a second probe portion, which specifically interacts with the target nucleic acid in close proximity to the first probe portion. Simultaneous binding of both probe portions to the target nucleic acid brings the first complementation molecule and the second complementation molecule into close proximity, such that their polypeptide portions are able to interact and form an assembled complementation complex, which can be detected by any means which allows recognition of the assembled complex but not the individual polypeptides.

In one particularly preferred embodiment, the first and the second probes bind to two adjacent sequences on the target nucleic acid, such that the first probe binds to a first target sequence and the second probe binds to a second target sequence. In this embodiment, the adjacent sequences are close enough to each other to allow the first and second polypeptides to interact when the first and second molecules are bound to the target, allowing assembly of the complementation complex. This embodiment provides for detection of single-stranded and double-stranded target nucleic acids. For detection of double stranded targets, the single-stranded probes interact with the double-stranded target to form a triplex.

In another particularly preferred embodiment, the first and the second probes are oligonucleotides and bind to the same sequence on a single-stranded target nucleic acid, forming a triplex. In this embodiment, the first and second polypeptides interact when the first and second molecules are bound to the target, allowing assembly of the complementation complex.

Complementation Complex Components

The complementation complex comprises a pair of complementation molecules, each of which is has a probe portion, for binding to the target nucleic acid, coupled to a polypeptide portion, for protein complementation. The individual polypeptides are inactive; however, binding of the pair of complementation molecules to the target nucleic acid in close proximity brings the two inactive polypeptide fragments together, allowing their re-association in to an active protein.

The polypeptide portions of each member of the complementation complex can be any polypeptides which associate when brought in to close proximity to generate a protein, which can be detected by any means which allows recognition of the assembled complex but not the individual polypeptides. For example, the two polypeptides may re-associate to generate a protein with enzymatic activity, to generate a protein with chromogenic or fluorogenic activity, or which create a protein recognized by an antibody.

The probe portion of each complementation molecule can be any molecule which allows binding to a target nucleic acid at a specific sequence. Preferred probe portions include nucleic acids, nucleic acid analogues, and polypeptides. In one preferred embodiment, the probe portion is an oligonucleotide. The probe portion of the complementation molecule is sometimes referred to simply as the probe. The probe portions of a given pair of complementation molecules can be of the same kind of molecule, for example oligonucleotides, or they can be different, for example one member of the pair has a nucleic acid probe, and the other member of the pair has a polypeptide probe.

The polypeptide portion and the probe portion of each complementation molecule can be coupled by any means which allows the polypeptide portion to interact with its corresponding polypeptide partner when the probe portion to bind to a target nucleic acid, allowing assembly of the complementation complex.

One particularly preferred embodiment of the present invention provides for detection of target nucleic acids in vivo. In this embodiment, the complementation molecules can be introduced into cells using any method which allows their localization at the appropriate site. Delivery methods include microinjection, liposome-mediated uptake, and in vivo synthesis of the complementation molecule by the cell to be targeted. Specific targeting can be achieved for example using subcellular localization markers, which target a protein to a specific compartment such as the nucleus or cytoplasm. Preferred methods include microinjection and in vivo synthesis of the complementation molecule by the cell to be targeted.

The present invention is directed to using protein complementation to detect the presence of a target nucleic acid, such as DNA or RNA. Previous uses of protein complementation have been used to look specifically at protein interactions, not nucleic acids. Nucleic acids have been used only to bring two polypeptides together to detect the presence of a protein. For example, the protein complementation assay of Michnick has been used to look directly at protein interactions, such as re-assembly of an enzyme, DHFR; Pelletier et al., *Proc. Natl. Acad. Sci. USA* 95: 12141-12146 (1998); U.S. Patent Application 20030049688. However, unlike the present invention, there is no nucleic acid component in Michnik, and the assay is not designed for detection of nucleic acids. Similarly, Landegren teaches a method of detecting an analyte using "proximity probes" which contain interacting proteins and nucleic acids. U.S. Patent Application No. 20020064779. However, unlike the present invention, in the Landegren approach, there is no protein complementation. Furthermore, the Landegren approach is essentially the opposite of the present invention, because the nucleic acids are brought into close proximity by the protein-protein interactions rather than the proteins being brought into close proximity by the nucleic acid interactions.

Polypeptide Portions of the Complementation Molecule

The polypeptide portions of each member of the complementation complex can be any polypeptides which associate when brought in to close proximity to generate a protein, which can be detected by any means which allows recognition of the assembled complex but not the individual polypeptides.

In one preferred embodiment of the invention, the first and second polypeptides interact in the complementation complex to form an assembled, active enzyme, which can be detected using an enzyme activity assay. Preferably, the enzyme activity is detected by a chromogenic or fluorogenic reaction. In one preferred embodiment, the enzyme is dihydrofolate reductase or β-lactamase.

In one preferred embodiment, the enzyme is dihydrofolate reductase (DHFR). For example, Michnick et al. have developed a "protein complementation assay" consisting of N- and C-terminal fragments of DHFR, which lack any enzymatic activity alone, but form a functional enzyme when brought into close proximity. See e.g. U.S. Pat. Nos. 6,428,951, 6,294,330, and 6,270,964, which are hereby incorporated by reference. Methods to detect DHFR activity, including chromogenic and fluoregenic methods, are well known in the art.

In another preferred embodiment of the invention, the first and second polypeptides interact in the complementation complex to form an assembled protein with detectable fluorogenic activity. In one preferred embodiment, the assembled protein is green fluorescent protein (GFP), a modified GFP such as EGFP, or any other natural or genetically engineered fluorescent protein including CFP, YFP, and RFP.

In another preferred embodiment of the invention, the first and second polypeptides interact in the complementation complex to form an assembled protein which contains a discontinuous epitope, which may be detected by use of an antibody which specifically recognizes the discontinuous epitope on the assembled protein but not the partial epitope present on either individual polypeptide. One such example of a discontinuous epitope is found in gp120 of HIV. These and other such derivatives can readily be made by the person of ordinary skill in the art based upon well known techniques, and screened for antibodies that recognize the assembled protein by neither protein fragment on its own.

In another embodiment of the invention, the molecules are proteins which interact to form an assembled protein. For example, the molecules may be protein fragments, or subunits of a dimer or multimer.

The codons used to synthesize the protein of interest may be optimized, converting them to codons that are preferentially used in a desired system. For example in mammalian cells. Optimal codons for expression of proteins in non-mammalian cells are also known, and can be used when the host cell is a non-mammalian cell (for example in insect cells).

The molecules bound to the probes of the present invention can contain any additional modifications which are desirable. For example, in one preferred-embodiment, the molecules may also comprise a flexible linker, which is coupled to the probe.

Probe Portions of the Complementation Molecule

The first probe portion and the second probe portion may be any molecules that can be coupled to another molecule, such as a polypeptide, and are capable of binding to a target nucleic acid in close proximity. In one preferred embodiment, the probes are nucleic acids or nucleic acid analogues, such as oligonucleotides. In another preferred embodiment of the present invention, one or both of the probe portions is a nucleic-acid binding polypeptide, which interacts with the target nucleic acid with high affinity. Other preferred nucleic acid analogues include peptide nucleic acids (PNAs), locked nucleic acids, morpholin DNAs, phosphorthioate DNAs, and 2'-O-methoxymethyl-RNAs.

One embodiment of the present invention provides for probe portions which are nucleic acids, which bind in close proximity to each other on the target nucleic acid. The first and second probe portion of the complementation molecules may bind to the same hybridization site on a single-stranded target, creating a triplex at the hybridization site. Alternatively, the first and second probe portion of the complementation molecules may bind to closely adjacent hybridization sites on a single-stranded or double-stranded target nucleic acid, creating either a duplex or a triplex at each hybridization site, respectively.

The length of the probe portion should be long enough to allow complementary binding to the nucleic acid target, and should allow the polypeptide portion of the first complementation molecule to interact with its corresponding polypeptide portion of the second complementation molecule when both probe portions are bound to the same target nucleic acid. For example, the probe can be 5-30 bases long. More preferably, 5-15 bases long.

In embodiments providing for formation of a triplex, the probe portion can be any nucleic acid which allows triplex formation. Preferred triplex-forming oligonucleotides are GC-rich. A preferred triplex is a purine triplex, consisting of pyrimidine-purine-purine.

One preferred triplex-forming oligonucleotide is GC-rich. A preferred triplex is a purine triplex, consisting of pyrimidine-purine-purine.

Preferred nucleic acid probe portions are oligonucleotides, single stranded RNA molecules, and peptide nucleic acids (PNAs) including pseudocomplementary PNAs (pcPNA).

In one preferred embodiment, the nucleic acid probe portions are oligonucleotides. Methods for designing and synthesizing oligonucleotides are well known in the art. Oligonucleotides are sometimes referred to as oligonucleotide primers.

Oligonucleotides useful in the present invention can be synthesized using established oligonucleotide synthesis methods. Methods of synthesizing oligonucleotides are well known in the art. Such methods can range from standard enzymatic digestion followed by nucleotide fragment isolation (see for example, Sambrook, et al., Molecular Cloning: A Laboratory Manual, Second Edition, Cold Spring Harbor, N.Y., (1989), Wu et al, Methods in Gene Biotechnology (CRC Press, New York, N.Y., 1997), and Recombinant Gene Expression Protocols, in Methods in Molecular Biology, Vol. 62, (Tuan, ed., Humana Press, Totowa, N.J., 1997), the disclosures of which are hereby incorporated by reference), to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method).

As used herein, the terms "oligonucleotide" and "primer" have the conventional meaning associated with it in standard nucleic acid procedures, i.e., an oligonucleotide that can hybridize to a polynucleotide template and act as a point of initiation for the synthesis of a primer extension product that is complementary to the template strand.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, Biochemistry 34:10807-10815 (1995), McGraw et al., Biotechniques 8:674-678 (1990), and Rychlik et al., Nucleic Acids Res. 18:6409-6412 (1990).

In one preferred embodiment, the nucleic acid probe portions are single stranded RNA molecules. Methods for designing and synthesizing single stranded RNA molecules are well known in the art.

In another preferred embodiment, the nucleic acid probe portions are peptide nucleic acids (PNAs), including pseudocomplementary PNAs (pcPNA). Methods for designing and synthesizing PNAs and pcPNAs are well known in the art. Peptide nucleic acids (PNAs) are analogs of DNA in which the backbone is a pesudopeptide rather than a sugar. Thus, their behavior mimics that of DNA and binds' complementary nucleic acid strands. In peptide nucleic acids, the deoxyribose phosphate backbone of oligonucleotides has been replaced with a backbone more akin to a peptide than a sugar phosphodiester. Each subunit has a naturally occurring or non naturally occurring base attached to this backbone. One such backbone is constructed of repeating units of N-(2-aminoethyl)glycine linked through amide bonds.

PNA binds both DNA and RNA. The resulting PNA/DNA or PNA/RNA duplexes are bound with greater affinity and increased specificity than corresponding DNA/DNA or DNA/RNA duplexes. In addition, their polyamide backbone (having appropriate nucleobases or other side chain groups attached thereto) is not recognized by either nucleases or proteases, and thus PNAs are resistant to degradation by enzymes, unlike DNA and peptides. The binding of a PNA strand to a DNA or RNA strand can occur in either a parallel of anti-parallel orientation. PNAs bind to both single stranded DNA and double stranded DNA.

To address the sequence limitations of traditional PNAs, pseudocomplementary PNAs (pcPNAs) have been developed. In addition to guanine and cytosine, pcPNA's carry 2,6-diaminopurine (D) and 2-thiouracil instead of adenine and thymine, respectively. pcPNAs exhibit a distinct binding mode, double-duplex invasion, which is based on the Watson-Crick recognition principle supplemented by the notion of pseudocomplentarity. pcPNAs recognize and bind with their natural A, T, (U), or G, C counterparts. pcPNAs can be made according to any method known in the art. For example, methods for the chemical assembly of PNAs are well known (See: U.S. Pat. No. 5,539,082, 5,527,675, 5,623,049, 5,714, 331, 5,736,336, 5,773,571 or 5,786,571, herein incorporated by reference).

Other embodiments of the invention provide a probe portion which is a polypeptide. The polypeptide can be any polypeptide with a high affinity for the target nucleic acid. In this embodiment, the target nucleic acid can be a double-stranded, triple-stranded, or single-stranded DNA or RNA. Preferably, the polypeptides is a peptide, less than 100 amino acids, or a full length protein. The polypeptide's affinity for the target nucleic acid can in the low nanomolar to high picomolar range. Preferred polypeptides include polypeptides which contain zinc fingers, either natural or designed by rational or screening approaches. Examples of zinc fingers include Zif 2g8, Sp1, finger 5 of Gfi-1, finger 3 of YY1, finger 4 and 6 of CF2II, and finger 2 of TTK (PNAS (2000) 97:1495-1500; J Biol Chem (20010 276 (21): 29466-78; Nucl Acids Res (2001) 29 (24):4920-9; Nucl Acid Res (2001) 29(11): 2427-36). Other preferred polypeptides include polypeptides, obtained by in vitro selection, that bind to specific nucleic acids sequences. Examples of such aptamers include platelet-derived growth factor (PDGF) (Nat Biotech (2002) 20:473-77) and thrombin (Nature (1992) 355: 564-6. Yet other preferred polypeptides are polypeptides which bind to DNA triplexes in vitro; examples include members of the heteronuclear ribonucleic particles (hnRNP) proteins such as hnRNP K, L, E1, A2/B1 and I (Nucl Acids Res (2001)29(11): 2427-36).

For complementation molecules which have a polypeptide for the probe portion, the entire complementation molecule can be encoded by a single construct, including the polypeptide portion, a linker and the probe portion which is also a polypeptide. This construct can either be expressed in the cell or microinjected into the cell. These constructs can also be used for in vitro detection of a nucleic acid of interest.

Coupling Mechanisms

The complementation molecules of the present invention have the polypeptide portion of the molecule coupled to the probe portion of the complementation molecule, such that when the probe portions of the first molecule and the second complementation molecules are bound to the target nucleic acid, the two polypeptides of the first and second complementation molecules can interact. The coupling mechanism for joining the probe portions to the polypeptides portions can be any mechanism which allows these interactions.

In one preferred embodiment, a flexible linker can be used to couple the probe portion and the polypeptide portion of the complementation molecule. In one preferred embodiment, the N-terminal amino acid and/or the C-terminal amino acid of each polypeptide is cysteine, and the probe has a thiol group at the 3' or 5' end, to allow coupling to the N-terminal and/or C-terminal cysteine. In another preferred embodiment, both the probe portion and the polypeptide portion are polypeptides, and they are coupled by N-terminal and/or C-terminal cysteines. In yet another preferred embodiment, a streptavidin-biotin interaction is used to couple the probe portion and the polypeptide portion of the complementation molecule.

Coupling may be accomplished by any chemical reaction that will bind the probe portion to the polypeptide portion, as long as the probe portion remains able to bind the hybridization site, and the polypeptide portion is able to interact with its partner to form an assembled molecule. This linkage can include for instance covalent binding, affinity binding, intercalation, coordinate binding and complexation. In one preferred embodiment, the coupling is performed in vitro and the binding is covalent. For example, for a protein, covalent binding can be achieved either by direct condensation of existing side chains or by the incorporation of external bridging molecules. Many bivalent or polyvalent linking agents are useful in coupling protein molecules to other molecules such as the probes of the present invention. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335-2549, 1984; Jansen, F. K., et al., 1 mm. Rev. 62:185-216, 1982; and Vitetta et al., supra).

Preferred linkers are described in the literature. See, for example, Ramakrishnan, S., et al., *Cancer Res.* 44: 201-208 (1984), describing the use of MBS (M-maleimidobenzoyl-N-hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS(N-hydroxysulfosuccinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In one preferred embodiment, the molecules are proteins which contain an N-terminal and/or C-terminal cysteine, which can be coupled to an oligonucleotide carrying a thiol group at either the 3' or 5'end and a donor or acceptor at the 5' or 3' end, respectively. In this embodiment it is desirable to substitute any other cysteines in the protein to other amino acids.

Nucleic Acid Target

The method of the present invention can be used to detect the presence of a single-stranded nucleic acid target or a double-stranded nucleic acid, by generating a detectable signal associated with formation of the complementation complex.

The nucleic acid target can be any nucleic acid which contains hybridization sites for binding to the first and second probes. For example, the target nucleic acid can be a DNA, an RNA, or a nucleic acid analogue.

The target nucleic acid can be single-stranded or double-stranded.

The target nucleic acid can be detected in vivo or in vitro. In one preferred embodiment, the method of the present invention is used to detect a target nucleic acid in vivo, and the polypeptides interact to generate a protein with fluorogenic activity. Preferably, the polypeptides encode GFP, a modified GFP such as EGFP, or any other natural or genetically engineered fluorescent proteins including CFP, YFP, and RFP.

In one particularly preferred embodiment, the first and the second probes bind to two adjacent sequences on the target nucleic acid, such that the first probe binds to a first target sequence and the second probe binds to a second target sequence. In this embodiment, the adjacent sequences are close enough to each other to allow the first and second polypeptides to interact when the first and second complementation molecules are bound to the target, allowing assembly of the complementation complex. This embodiment provides for detection of single-stranded and double-stranded target nucleic acids. For detection of double stranded targets, the single-stranded probes interact with the double-stranded target to form a triplex.

In another particularly preferred embodiment, the first and the second probes are oligonucleotides and bind to the same sequence on a single-stranded target nucleic acid, forming a triplex. In this embodiment, the first and second polypeptides interact when the first and second complementation molecules are bound to the target, allowing assembly of the complementation complex.

Any nucleic acid sample may be used in practicing the present invention, including without limitation eukaryotic, prokaryotic and viral DNA or RNA. In a preferred embodiment, the target nucleic acid represents a sample of genomic DNA isolated from a patient. This DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, semen and tissue exudates at the site of infection or inflammation. In one preferred embodiment, the DNA is detected directly in the sample, without any additional purification. In another embodiment, the DNA is extracted from the cell source or body fluid using any of the numerous methods that are standard in the art. It will be understood that the particular method used to extract DNA will depend on the nature of the source. The preferred amount of DNA to be extracted for use in the present invention is at least 5 pg (corresponding to about 1 cell equivalent of a genome size of 4×109 base pairs).

In one preferred embodiment, the target nucleic acid can be amplified prior to exposure to the components of the complementation complex. Any method of amplifying a nucleic acid target can be used, including methods which generate a single stranded nucleic acid with a multiplicity of the same hybridization sites. The amplification reaction can be polymerase chain reaction (PCR), ligase chain reaction (LCR), strand displacement amplification (SDA), transcription mediated amplification (TMA), Qβ-replicase amplification (Q-beta), or rolling circle amplification (RCA).

In one preferred embodiment, PCR is used to amplify the nucleic acid target.

Any polymerase which can synthesize the desired nucleic acid may be used. Preferred polymerases include but are not limited to Sequenase, Vent, and Taq polymerase. Preferably, one uses a high fidelity polymerase (such as Clontech HF-2) to minimize polymerase-introduced mutations.

In another preferred embodiment, rolling circle amplification (RCA) is used to generate a single-stranded DNA target with a multiplicity of the same hybridization sites. Rolling circle amplification (RCA) is an isothermal process for generating multiple copies of a sequence. In rolling circle DNA replication in vivo, a DNA polymerase extends a primer on a circular template (Kornberg, A. and Baker, T. A. DNA Replication, W. H. Freeman, New York, 1991). The product consists of tandemly linked copies of the complementary sequence of the template. RCA is a method that has been adapted for use in vitro for DNA amplification (Fire, A. and Si-Qun Xu, Proc. Natl. Acad. Sci. USA, 1995, 92:4641-4645; Lui, D., et al., J. Am. Chem. Soc., 1996, 118:1587-1594; Lizardi, P. M., et al., Nature Genetics, 1998, 19:225-232; U.S. Pat. No. 5,714,320 to Kool).

In RCA techniques a primer sequence having a region complementary to an amplification target circle (ATC) is combined with an ATC. Following hybridization, enzyme, dNTPs, etc. allow extension of the primer along the ATC template, with DNA polymerase displacing the earlier segment, generating a single stranded DNA product which consists of repeated tandem units of the original ATC sequence.

RCA techniques are well known in the art, including linear RCA (LRCA). Any such RCA technique can be used in the present invention. Strand displacement during RCA can be facilitated through the use of a strand displacement factor, such as helicase. In general, any DNA polymerase that can perform rolling circle replication in the presence of a strand displacement factor is suitable for use in the processes of the present invention, even if the DNA polymerase does not perform rolling circle replication in the absence of such a factor. Strand displacement factors useful in RCA include BMRF1 polymerase accessory subunit (Tsurumi et al., J. Virology 67(12):7648-7653 (1993)), adenovirus DNA-binding protein (Zijderveld and van der Vliet, J. Virology 68(2):1158-1164 (1994)), herpes simplex viral protein ICP8 (Boehmer and Lehman, J. Virology 67(2):711-715 (1993); Skaliter and Lehman, Proc. Natl. Acad. Sci. USA 91(22):10665-10669 (1994)), single-stranded DNA binding proteins (SSB; Rigler and Romano, J. Biol. Chem. 270:8910-8919 (1995)), and calf thymus helicase (Siegel et al., J. Biol. Chem. 267:13629-13635 (1992)). The ability of a polymerase to carry out rolling circle replication can be determined by using the polymerase in a rolling circle replication assay such as those described in Fire and Xu, Proc. Natl. Acad. Sci. USA 92:4641-4645 (1995) and in Lizardi (U.S. Pat. No. 5,854,033, e.g., Example 1 therein).

Applications

The method of the present invention can be used to detect the presence of a target nucleic acid of interest either in vivo or in vitro. Because the methods, kits and compositions of this invention are directed to the specific detection of target nucleic acid, even in the presence of non-target sequences, they are particularly well suited for the development of sensitive and reliable probe-based hybridization assays designed to analyze for point mutations. The methods, kits and compositions of this invention are also useful for the detection, quantitation or analysis of organisms (micro-organisms), viruses, fungi and genetically based clinical conditions of interest.

In one embodiment, the present invention provides methods for isolating a target nucleic acid in a sample, even in the presence of non-target sequences.

One embodiment of the invention provides for the use of the complementation molecules to screen for a target nucleic acid. For example, to identify a target nucleic acid of interest in a population of other non-target nucleic acids. In this embodiment, the target nucleic acids or the complementation molecules of the present invention can be used in a form in which they are attached, by whatever means is convenient, to some type of solid support. Attachment to such supports can be by means of some molecular species, such as some type of polymer, biological or otherwise, that serves to attach said primer or ATC to a solid support so as to facilitate detection of tandem sequence DNA produced by rolling circle amplification using the methods of the invention.

Such solid-state substrates useful in the methods of the invention can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a glass slide or a microtiter dish. (for example, the standard 96-well dish). For additional arrangements, see those described in U.S. Pat. No. 5,854,033.

Methods for immobilization of oligonucleotides to solid-state substrates are well established. Oligonucleotides, including address probes and detection probes, can be coupled to substrates using established coupling methods. For example, suitable attachment methods are described by Pease et al., Proc. Natl. Acad. Sci. USA 91(11):5022-5026 (1994). A preferred method of attaching oligonucleotides to solid-state substrates is described by Guo et al., Nucleic Acids Res. 22:5456-5465 (1994).

In another preferred embodiment, the present invention provides kits suitable for detecting the presence and/or amount of a target nucleic acid in a sample. Said kits comprise at least a first probe coupled to a first molecule and a second probe coupled to a second molecule, wherein the probes can bind to a hybridization sequence in a target nucleic acid. Preferably, the probes are in vials. Said kits also comprise reagents suitable for capturing and/or detecting the present or amount of target nucleic acid in a sample. The reagents for detecting the present and/or amount of target nucleic acid can include enzymatic activity reagents or an antibody specific for the assembled protein. The antibody can be labeled. Such kits may optionally include the reagents required for performing RCA reactions, such as DNA polymerase, DNA polymerase cofactors, and deoxyribonucleotide-5'-triphosphates. Optionally, the kit may also include various polynucleotide molecules, DNA or RNA ligases, restriction endonucleases, reverse transcriptases, terminal transferases, various buffers and reagents, and antibodies that inhibit DNA polymerase activity. These components are in containers, such as vials. The kits may also include reagents necessary for performing positive and negative control reactions, as well as instructions. Optimal amounts of reagents to be used in a given reaction can be readily determined by the skilled artisan having the benefit of the current disclosure.

The target nucleic acid can be of human origin. The target nucleic acid can be DNA or RNA. The target nucleic acid can be free in solution or immobilized to a solid support.

In one embodiment, the target nucleic acid is specific for a genetically based disease or is specific for a predisposition to a genetically based disease. Said diseases can be, for example, .beta.-Thalassemia, Sickle cell anemia or Factor-V Leiden, genetically-based diseases like cystic fibrosis (CF), cancer related targets like p53 and p10, or BRC-1 and BRC-2 for breast cancer susceptibility. In yet another embodiment, isolated chromosomal DNA may be investigated in relation to paternity testing, identity confirmation or crime investigation.

The target nucleic acid can be specific for a pathogen or a microorganism. Alternatively, the target nucleic acid can be from a virus, bacterium, fungus, parasite or a yeast; wherein hybridization of the complementation molecules to the target nucleic acid is indicative of the presence of said pathogen or microorganism in the sample.

The target nucleic acid may also be useful for the detection of bacteria and eucarya in food, beverages, water, pharmaceutical products, personal care products, dairy products or environmental samples. Preferred beverages include soda, bottled water, fruit juice, beer, wine or liquor products. Assays developed will be particularly useful for the analysis of raw materials, equipment, products or processes used to manufacture or store food, beverages, water, pharmaceutical products, personal care products, dairy products or environmental samples.

EXAMPLES

Example 1

DNA-Assisted Protein Complementation Using 21-Mer Complementary Oligonucleotides as Interacting Partners and Enhanced Green Fluorescent Protein (EGFP)

DNA assisted protein complementation was assayed by mixing two protein-DNA hybrids based on the Enhanced Green Fluorescent Protein (EGFP) molecule. The following steps were done to perform the experiments.

Cloning, Expression and Purification of Polypeptides

The following genes were obtained by PCR and cloned in the TWIN-1 vector (New England Biolabs, MA), as C-terminal fusion of Ssp DNAB intein. Construct 1: Full EGFP-1 (Clontech, CA). Construct 2: α-cys polypeptide containing the 157 amino acid N-terminal portion of EGFP, plus a C-terminal cysteine. Construct 3: β-cys fragment polypeptide containing the remaining 82 amino acid C-terminal portion of EGFP, plus an N-terminal cysteine. These constructs were verified by sequencing.

The proteins were expressed in BL21(DE3)pLys competent cells (Stratagene, CA). Induction was done with IPTG and cells were allowed to grow for 4 hrs at 30° C. Cells were lysed in Buffer S (50 mM HEPES pH 8.5, 0.5 M NaCl, 1 mM EDTA, 10 mM DTT, Triton X-100 0.1%. 1 mM PMSF) by freeze and thaw method. After DNAse I treatment, samples were centrifuged at 13000 g for 30 minutes at 4° C. The supernatants were applied to a chitin affinity chromatography resin (New England Biolabs, MA) equilibrated with Buffer B (50 mM HEPES pH 8.5, 0.5 M NaCl, 1 mM EDTA, 10 mM DTT, Triton X-100 0.1%. 0.5 mM PMSF). After that, the column was washed extensively with the same buffer. Then the column was equilibrated in Buffer E (50 mM HEPES pH 7.0, 0.5 M NaCl, 1 mM EDTA, 10 mM DTT, Triton X-100 0.1%. 0.5 mM PMSF) and let at 4° C. for 24-48 hrs for the intein cleavage to take place. In the next step, eluates were collected and protein concentration and purity were analyzed by SDS-PAGE and Coomasie Plus Protein Assay Reagent (Pierce, Ill.).

Conjugation of the EGFP Fragments with the Oligonucleotides

DNA oligonucleotides with an $SH_2$ group at either the 5 or 3' end were purchased from Integrated DNA Technologies, IO. The oligonucleotides have the following sequences: Oligonucleotide B1: 5'-SH2-C6—CGACTGCGTTAGCATGT-GTTG-3' (SEQ ID NO:1). "C6" is a 6 carbon spacer. Oligonucleotide B2: 5'-GCTGACGCAATCGTACACAAC-C3-C3-SH2-3' (SEQ ID NO:2). B2 is complementary and parallel to B1. "C3" is a 3 carbon spacer. Oligonucleotide AP-B2: 5'-SH2-C6—CAACACATGCTAACGCAGTCG-3' (SEQ ID NO:3). AP-B2 is complementary and antiparallel to B1.

The protein fragments (1.6 uM) were mixed with an excess of oligonucleotides (50 uM) in 500 ul of Buffer M (50 mM HEPES pH 7.0, 0.5 M NaCl, 1 mM EDTA, DTT 10 mM, PMSF 0.5 mM, 10 mM Tris-Cl). They were paired as follows: α-cys fragment plus oligonucleotide B1. (α-B1, also referred to as AC-B1). β-cys fragment plus oligonucleotide B2. (β-B2, also referred to as BC-B2). β-cys fragment plus oligonucleotide APB2. (β-APB2, also referred to as BC-APB2). β-cys fragment plus oligonucleotide B1. (β-B1, also referred to as BC-B1).

After mixing the samples, they were kept on ice for 3-4 hours. Afterwards, the samples were applied to a NAP-5 column (Sephadex G-25 Medium DNA-grade) (Pharmacia) at room temperature by gravity flow, to remove the DTT and thus activate the SH2 groups in both molecules. The column was equilibrated with Buffer C (50 mM HEPES pH 7.0, 0.5 M NaCl, 1 mM EDTA, PMSF 0.5 mM). Fractions were analyzed by UV spectroscopy at 260 and 280 m.

Results

FIG. 1 shows a typical chromatographic profile of 1/10 diluted samples from a conjugation experiment. In FIG. 1, the chromatographic profile of a conjugation mixture (Alpha-cys plus oligonucleotide B1) on a Sephadex G-25 column. Alpha-cys fragment (1.6 uM) was mixed with oligonucleotide B1 (50 uM) in 500 ul of buffer M (50 mM HEPES pH 7.0, 0.5 M NaCl, 1 mM EDTA, 10 mM DTT, 0.5 mM PMSF, 10 mM Tris-Cl) and left on ice for 3-4 hrs is shown. Afterwards, the sample was applied by gravity flow to a G-25 Sephadex column (NAP-5, Pharmacia) equilibrated with buffer C (50 mM HEPES pH 7.0, 0.5 M NaCl, 1 mM EDTA, 0.5 mM PMSF). Fractions (~0.17 ml)) were collected at room temperature.

The chromatographic profiles were similar in all the conjugation experiments. Samples from the beginning of the first peak (usually fraction #4) were concentrated about 3 times in a centricon (Millipore, MA) at 4° C. Filters with a 10 KD cut-off were used for the Alpha-DNA hybrids and filters with a 3 KD cut-off were used for the Beta-DNA hybrids.

Reconstitution of Functional EGFP Via a DNA-DNA Interaction

In a typical experiment, one protein-DNA hybrid (Alpha-B1 for instance) is mixed in equal volume (7.5 ul each hybrid) with its counterpart (Beta-B2) in a 1.5 ml microfuge tube. Immediately afterwards, this mix is added to 300 ul of buffer F (20 mM Tris-Cl ph 8.0, 50 mM NaCl, 0.1% Triton X-100) already in the cuvette. The solution is mixed by inversion twice and placed in the fluorimeter.

Excitation was made at 488 nm and the emission spectra recorded between 490 and 550 nm. Scan speed was 60 nm/min, the excitation and emission slits were set at: 10 nm and the PMT voltage was 700 volts. Fluorescence measurements were done in a Spectrophotometer FL F-2500 fluorimeter (Hitachi) at room temperature. Samples were kept on ice before and after experiments.

Several controls were included in the experiments: a) Full EGFP; b) Alpha-cys and Beta-cys fragments without DNA, separately and combined; and c) Paired DNA oligonucleotides (B1-B2, B1-APB2) without proteins.

Figure 2:
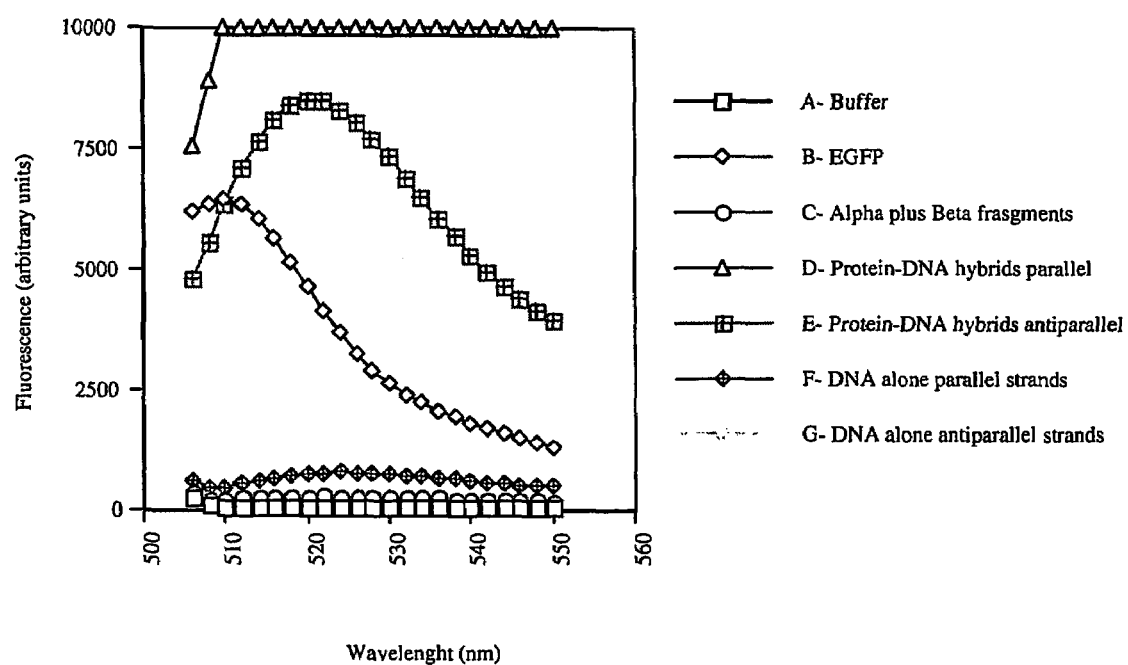
FIG. 2 shows the results of DNA assisted protein complementation. Mixing two fragments of EGFP subjected to conjugation with complementary DNA oligonucleotides restores fluorescent activity of the protein.

FIG. 2 shows the fluorescence spectra of full EGFP, and different mixtures of Alpha-cys and Beta-cys fragments and the conjugated protein-DNA fragments with the B1, B2 and APB2 oligonucleotides. These results show that the combination of the Alpha fragment of EGFP subjected to conjugation with the B1 oligonucleotide (Alpha-B1 hybrid) and the Beta fragment of EGFP subjected to conjugation with the complementary antiparallel oligonucleotide APB2 (Beta-APB2 hybrid) generated a fluorescence significantly above background. Unexpectedly, we also observed a strong fluorescence signal when the Alpha-B1 hybrid was mixed with the Beta fragment of EGFP subjected to conjugation with the B2 oligonucleotide (Beta-B2 hybrid), which is parallel to the B1 oligonucleotide.

In a separate series of experiments, it was shown that using the same oligonucleotide (B1) conjugated with both the Alpha-cys and Beta-cys fragments of EGFP did not produce a fluorescent signal above the background given by the protein fragments alone.

Figure 3:
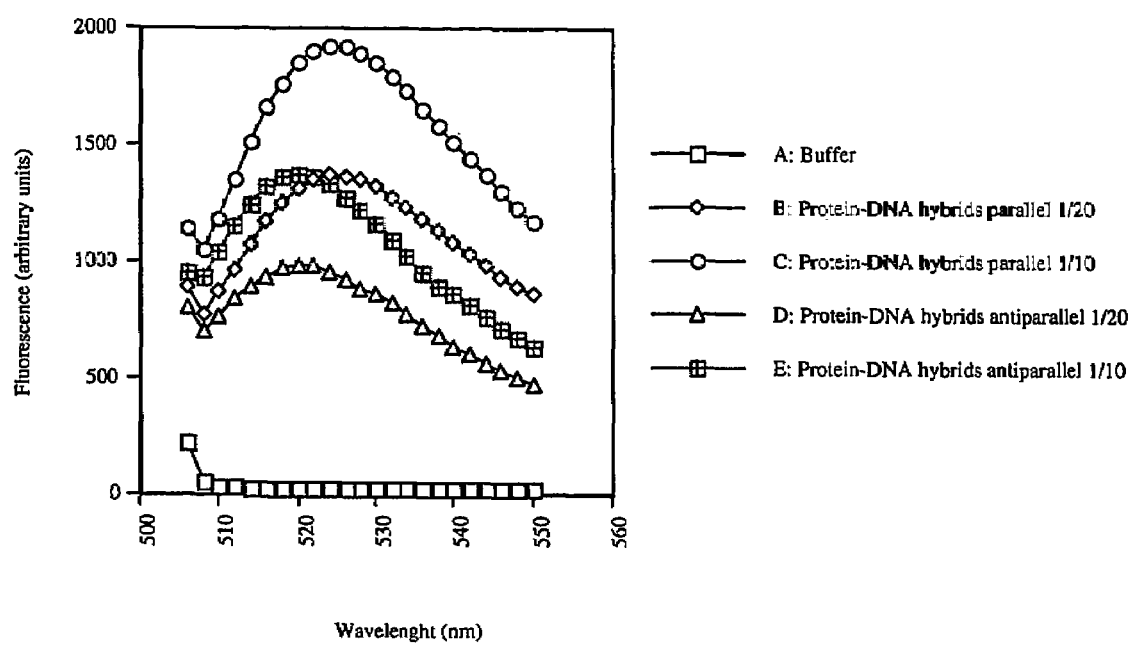
FIG. 3 shows the results of parallel versus antiparallel orientation and stability of a DNA assisted protein complementation assay. 24 hours after the initial measurements described in FIG. 2, the mixtures that produced fluorescence (Alpha-DNA plus Beta-DNA hybrids) were serially diluted in buffer F (20 mM Tris-Cl, pH 8.0, 50 mM NaCl, 0.1% Triton X-100) and assayed for fluorescence.

FIG. 3 shows the difference in maximum between parallel and antiparallel orientations of the DNA oligonucleotides. It should be emphasized that the complexes are stable at 4° C. since the spectra shown in FIG. 3 were recorded 24 hours after the complementation experiments.

FIG. 3 shows the results of parallel versus antiparallel orientation and stability of a DNA assisted protein complementation assay. 24 hours after the initial measurements described in FIG. 2, the mixtures that produced fluorescence (Alpha-DNA plus Beta-DNA hybrids) were serially diluted in buffer F (20 mM Tris-Cl, pH 8.0, 50 mM NaCl, 0.1% Triton X-100) and assayed for fluorescence. FIG. 3A: Buffer. FIG. 3B: Alpha hybrid containing oligonucleotide B1 mixed in equal volume (7.5 μl) with Beta hybrid containing a parallel complementary oligonucleotide (B2) diluted ½0. FIG. 3C: Alpha hybrid containing oligonucleotide B1 mixed in equal volume (7.5 μl) with Beta hybrid containing a parallel complementary oligonucleotide (B2) diluted ½0. FIG. 3E: Alpha hybrid containing oligonucleotide B1 mixed in equal volume (7.5 μl) with Beta hybrid containing an antiparallel complementary oligonucleotide (APB2) diluted ½0. FIG. 3E: Alpha hybrid containing oligonucleotide B1 mixed in equal volume (7.5 μl) with Beta hybrid containing an antiparallel complementary oligonucleotide (APB2) diluted ½0.

These experiments show that the presence in the mixture of protein-DNA hybrids with complementary oligonucleotides is necessary to produce a fluorescence signal above the background. This shows the feasibility of a protein complementation driven by DNA-DNA interactions provided by complementarity of 21 mer DNA duplexes. A more detailed biochemical characterization of the DNA-assisted protein complementation reaction is being done at our lab at the moment.

Example 2

Figure 4:
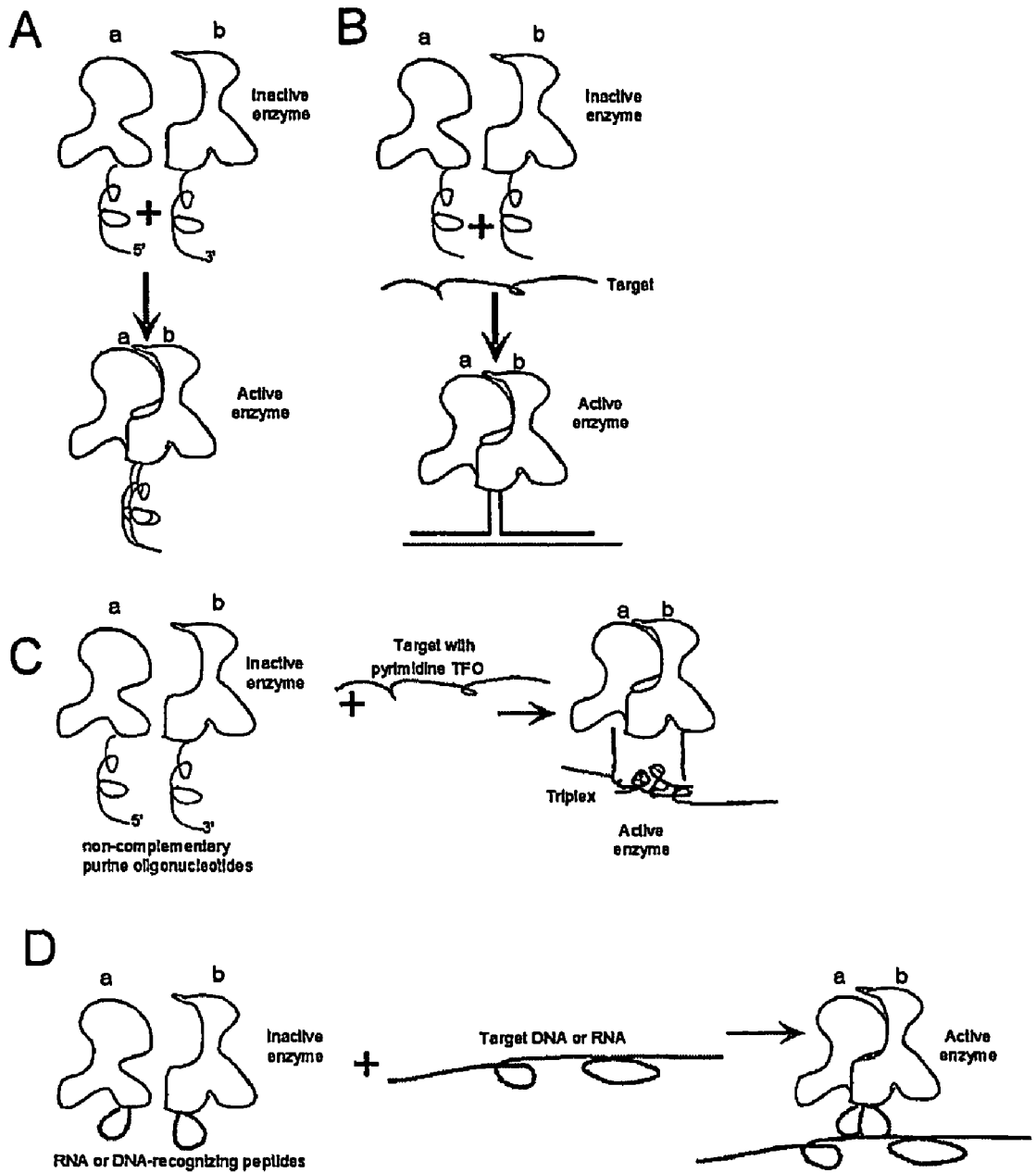
FIG. 4 depicts several schematics of the protein-complementation assay supported by nucleic acid interactions. Proteins or protein fragments are labeled with short oligonucleotides capable of duplex or triplex complex formation. The design of the oligonucleotide probes allows their complementary interactions or triplex formation.
Figure 5:
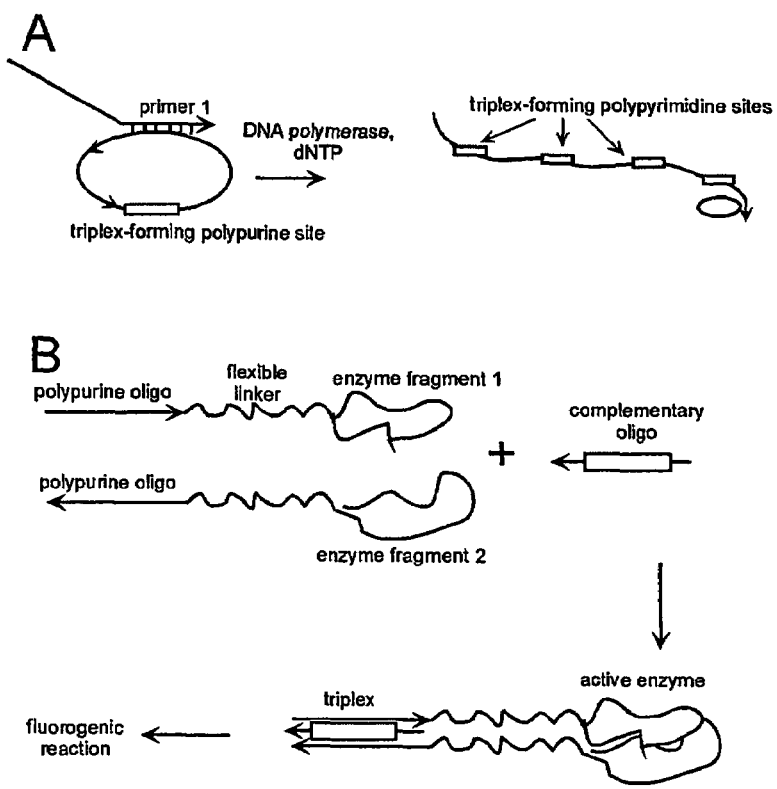
FIG. 5 depicts the protein-complementation assay supported by triplex DNA formation and applied in rolling circle amplification (RCA).

Protein-Complementation Assay Supported by Triplex DNA Formation and Applied in Rolling Circle Amplification The general purpose of the present invention consists of developing a new universal and robust method for detection of DNA and RNA targets. The method can be also used in protein-protein interaction studies. One embodiment of the invention utilizes the protein fragment complementation assay (PCA). PCA relies on re-association of two inactive protein fragments into an active enzyme if and only if there are additional interactions assisting protein re-association. In the original PCA method developed by Michnick these are protein-protein interactions, which support re-association of the marker enzyme (1). In our method, the enzyme activity relies on DNA-DNA or DNA-RNA or RNA-RNA interactions (FIGS. 4 and 5).

In one embodiment, a single-stranded DNA target is detected in the presence of two triplex forming oligonucleotides coupled with the inactive enzyme fragments such as dihydrofolate reductase, DHFR, or β-lactamase (FIG. 5), or two inactive protein fragments such as EGFP (FIGS. 1-3). The triplex-forming oligonucleotide is GC-rich to make relatively stable complex. Purine triplexes (PyPuPu) fit most our purposes, because they are stable enough at neutral pH (2).

In this embodiment, linear rolling circle amplification (RCA) is performed to generate single-stranded DNA product (3,4). The active enzyme is assembled from the fragments in the presence of the increasing amount of triplex-forming sequence produced by RCA, and its activity is detected by chromogenic or fluorogenic reaction. This assay differs substantially from the classic RCA because in this case, signal amplification is mostly gained by the enzymatic activity of the re-assembled protein. This format will allow for faster analysis then in conventional RCA and sensitivity comparable with hyper-branched RCA.

To reduce this approach to practice, we will use N- and C-terminal fragments of dihydrofolate reductase (DHFR), the system developed by S. Michnick (Pelletier et al., 1998). We will synthesize DHFR peptides in vivo by expressing the corresponding plasmids in *E. coli*. Each plasmid will code for the DHFR fragment, flexible peptide linker attached to the N-terminus, and the His-tag at the C-terminus. The N-terminal amino acid will be designed to be cystein (the only cystein in DHFR, $C_7$, will be substituted for Thr). The plasmids coding for the fragments of DHFR are available from the Michnick's lab. They will be modified if necessary by using PCR with corresponding primers. The peptides will be purified from *E. coli* cell lysates and coupled with oligonucleotides carrying thiol-group at the 3'- or 5'-end and donor or acceptor at the 5' or 3' end, respectively. The by-products oligonucleotide- and peptide-dimers will be removed.

REFERENCES

All references described herein are incorporated herein by reference.

1. Pelletier J N, Campbell-Valois F X, Michnick S W. (1998) Oligomerization domain-directed reassembly of active dihydrofolate reductase from rationally designed fragments. *Proc Natl Acad Sci USA* 95, 12141-12146.
2. Frank-Kamenetskii M D, Mirkin S M. (1995) Triplex DNA structures. *Annu Rev Biochem.* 64, 65-95.
3. Fire A, Xu S-Q. (1995) Rolling amplification of short DNA circles. *Proc Natl Acad Sci USA* 92, 4641-4645.
4. Sabanayagam C R, Berkey C, Lavi U, Cantor C R, Smith C L (1999) Molecular DNA switches and chips. In Ferrari M. (ed). *Micro- and Nanofabricated Structures and Devices for Biomedical and Environmental Applications II. Proceedings SPIE* (The international Society for Optical Engineering), vol. 3606, pp. 90-97.
5. Fredriksson S, Gullberg M, Jarvius J, Olsson C, Pietras K, Gustafsdottir S M, Ostman A, Landegren U. (2002) Protein detection using proximity-dependent DNA ligation assays. *Nat Biotechnol.* 20:473-7.
6. Niemeyer C M, Koehler J, Wuerdemann C. (2002) DNA-directed assembly of bi-enzymic complexes from in vivo biotinylated NAD(P)H:FMN oxidoreductase and luciferase. *Chembiochem.* 3(2-3): 242-5.
7. Ozawa T, Nogami S, Sato M, Ohya Y, Umezawa Y. (2000) A fluorescent indicator for detecting protein-protein interactions in vivo based on protein splicing. *Anal Chem.* 72, 5151-7.
8. Ozawa T, Takeuchi T M, Kaihara A, Sato M, Umezawa Y. (2001) Protein splicing-based reconstitution of split green fluorescent protein for monitoring protein-protein interactions in bacteria: improved sensitivity and reduced screening time. *Anal Chem* 73, 5866-74.
9. Ozawa T, Kaihara A, Sato M, Tachihara K, Umezawa Y. (2001) Split luciferase as an optical probe for detecting protein-protein interactions in mammalian cells based on protein splicing. *Anal Chem.* 73, 2516-21.
10. Ainger K, Avossa D, Diana A S, Barry C, Barbarese E, Carson J H. (1997) Transport and localization elements in myelin basic protein mRNA. *J. Cell Biol.* 138(5):1077-87.
11. Bassell G J, Oleynikov Y, Singer R H. (1999) The travels of mRNAs through all cells large and small. *FASEB J.* 13(3):447-54.
12. Beach D L, Salmon E D, Bloom K. (1999) Localization and anchoring of mRNA in budding yeast. *Curr Biol.* 9(11):569-78.
13. Bertrand E, Chartrand P, Schaefer M, Shenoy S M, Singer R H, Long R M. (1998) Localization of ASH1 mRNA particles in living yeast. *Mol Cell.* 2 (4):437-45.
14. Carmo-Fonseca M, Custodio N, Calado A. (1999) Intranuclear trafficking of messenger RNA. *Crit Rev Eukaryot Gene Expr.* 9(3-4):213-9.
15. Johnston D S (1995) The intracellular localization of messenger RNA. *Cell* 81, 161-170.
16. Matsuo T. (1998) In situ visualization of messenger RNA for basic fibroblast growth factor in living cells. *Biochim Biophys Acta* 1379 (2):178-84.
17. Molenaar C, Marras S A, Slats J C, Truffert J C, Lemaitre M, Raap A K, Dirks R W, Tanke H J. (2001) Linear 2' O-Methyl RNA probes for the visualization of RNA in living cells. *Nucleic Acids Res.* 29(17):E89-9.
18. Oleynikov Y, Singer R H. (2003) Real-time visualization of ZBP1 association with beta-actin mRNA during transcription and localization. *Cur Biol.* 13(3):199-207.
19. Pederson, T. (2001) Fluorescent RNA cytochemistry: tracking gene transcripts in living cells. *Nucleic Acids Res.* 29(5): 1013-6.
20. Perlette J, Tan W. (2001) Real-time monitoring of intracellular mRNA hybridization inside single living cells. *Anal Chem.* 73 (22):5544-50.
21. Politz J C. (1999) Use of caged fluorochromes to track macromolecular movement in living cells. *Trends Cell Biol.* 9 (7):284-7
22. Politz J C, Taneja K L, Singer R H. (1995) Characterization of hybridization between synthetic oligodeoxynucleotides and RNA in living cells. *Nucleic Acids Res.* 23(24): 4946-53.
23. Sando S, Kool E T. (2002) Imaging of RNA in bacteria with self-ligating quenched probes. *J Am Chem Soc.* 124 (33):9686-7.
24. Sei-Iida Y, Koshimoto H, Kondo S, Tsuji A. (2000) Real-time monitoring of in vitro transcriptional RNA synthesis using fluorescence resonance energy transfer. *Nucleic Acids Res.* 28(12):E59.
25. Sokol, D. L., Zhang, X., Lu, P., Gewirtz, A. M. (1998) Real time detection of DNA/RNA hybridization in living cells. *Proc Natl Acad Sci USA.* 95, 11538-11543.
26. Tan, W., Fang, X., Li, J., Liu, X. (2000) Molecular beacons: a novel DNA probe for nucleic acid and protein studies. *Chemistry,* 6, 1107-1111.
27. Molenaar C, Marras S A, Slats J C, Truffert J C, Lemaitre M, Raap A K, Dirks R W, Tanke H J. (2001) Linear 2' O-Methyl RNA probes for the visualization of RNA in living cells. *Nucleic Acids Res.* 29(17):E89-9.

28. Tsuji A, Sato Y, Hirano M, Suga T, Koshimoto H, Taguchi T, Ohsuka S. (2001) Development of a time-resolved fluorometric method for observing hybridization in living cells using fluorescence resonance energy transfer. *Biophys J.* 81(1):501-15.
29. Tsuji A, Koshimoto H, Sato Y, Hirano M, Sei-Iida Y, Kondo S, Ishibashi K. (2000) Direct observation of specific messenger RNA in a single living cell under a fluorescence microscope. *Biophys J.* 78(6):3260-74.

We claim:

1. A method for the detection of a target nucleic acid molecule in a living cell, comprising:
   a) exposing the target nucleic acid molecule to a first complementation molecule and a second complementation molecule, wherein the first complementation molecule comprises a first polypeptide portion coupled to a first probe portion, wherein the first probe portion binds to a first nucleic acid hybridization-site, and wherein the second complementation molecule comprises a second polypeptide portion coupled to a second probe portion, wherein the second probe portion binds to a second nucleic acid hybridization site, and wherein the first and second probe portions are nucleic acids or nucleic acid analogues, and wherein when the first and second probe portions hybridize to nucleic acid sites that are located in close proximity to each other, then the first and second polypeptide portions of the first and second complementation molecules interact and form an assembled complementation complex;
   b) allowing the components to react under conditions that permit the formation of an assembled complementation complex; and
   c) determining if an assembled complementation complex is present by any means which allows detection of the assembled complex but not the individual polypeptide portions;
   wherein the presence of an assembled complex shows the target nucleic acid in the living cell.

2. The method of claim 1, wherein the first and second polypeptides interact in the complementation complex to form an active enzyme.

3. The method of claim 1, wherein the first and second polypeptides interact in the complementation complex to form an assembled protein with detectable fluorogenic activity.

4. The method of claim 1, wherein the first and second polypeptides interact in the complementation complex to form an assembled protein which contains a discontinuous epitope, which may be detected by use of an antibody which specifically recognizes the discontinuous epitope on the assembled protein but not the partial epitope present on either individual polypeptide.

5. The method of claim 1, wherein the target nucleic acid is detected in vivo or in vitro.

6. The method of claim 5, wherein the target nucleic acid is detected in vivo.

7. The method of claim 1, wherein the target nucleic acid is single-stranded or double-stranded.

8. The method of claim 2, wherein the active enzyme is detected by a chromogenic or fluorogenic reaction.

9. The method of claim 8, wherein the enzyme is dihydrofolate reductase or β-lactamase.

10. The method of claim 3, wherein the assembled protein is a fluorescent protein.

11. The method of claim 10, wherein the fluorescent protein is a natural, modified, or genetically engineered fluorescent protein.

12. The method of claim 11, wherein the fluorescent protein is selected from the group consisting of GFP, EGFP, CFP, YFP, and RFP.

13. The method of claim 1, wherein the first probe portion and the second probe portion are oligonucleotides.

14. The method of claim 1, wherein the probe portion and the polypeptide portion of each complementation molecule is coupled by a flexible linker.

15. The method of claim 1, wherein the target nucleic acid is amplified prior to exposure to the first and second complementation molecules.

16. The method of claim 15, wherein the target nucleic acid is amplified using rolling circle amplification to generate a single-stranded DNA target with a multiplicity of the same hybridization sites.

17. The method of claim 1, wherein the first and the second probes bind to two adjacent sequences in the target nucleic acid.

18. The method of claim 1, wherein the first and the second probes bind to the same sequence in the target nucleic acid to form a triplex, wherein the target nucleic acid sequence forms part of the triplex.

19. A kit for the detection of a target nucleic acid molecule in a living cell, wherein the kit comprises a vial containing a first complementation molecule and a vial containing a second complementation molecule, wherein the first complementation molecule comprises a first polypeptide portion coupled to a first probe portion, wherein the first probe portion binds to a first nucleic acid hybridization site of the target nucleic acid molecule in the living cell, and wherein the second complementation molecule comprises a second polypeptide portion coupled to a second probe portion, wherein the second probe portion binds to a second nucleic acid hybridization site of the target nucleic acid molecule in the living cell, and wherein the first and second probe portions are nucleic acids or nucleic acid analogues, and wherein when the first and second probe portions bind to nucleic acid sites that are located in close proximity to each other, then the first and second polypeptide portions of the first and second complementation molecules interact and form an assembled complementation complex when the target nucleic acid molecule in the living cell is exposed to the first and second complementation molecules.

20. The kit of claim 19, wherein the first and second polypeptides interact in the complementation complex to form an active enzyme.

21. The kit of claim 19, wherein the first and second polypeptides interact in the complementation complex to form an assembled protein with detectable fluorogenic activity.

22. The kit of claim 19, wherein the first and second polypeptides interact in the complementation complex to form an assembled protein which contains a discontinuous epitope, which may be detected by use of an antibody which specifically recognizes the discontinuous epitope on the assembled protein but not the partial epitope present on either individual polypeptide.

23. The method of claim 1, wherein the living cell is in vivo.

24. The method of claim 1, wherein the living cell is in vitro.

* * * * *

UNITED STATES PATENT AND TRADEMARK OFFICE
CERTIFICATE OF CORRECTION

PATENT NO. : 7,662,554 B2 Page 1 of 1
APPLICATION NO. : 10/529122
DATED : February 16, 2010
INVENTOR(S) : Cantor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 271 days.

Signed and Sealed this

Thirtieth Day of November, 2010

David J. Kappos
*Director of the United States Patent and Trademark Office*